US00PP23590P2

(12) United States Plant Patent
Korlipara

(10) Patent No.: US PP23,590 P2
(45) Date of Patent: May 7, 2013

(54) ***RUDBECKIA* PLANT NAMED 'LITTLE HENRY'**

(50) Latin Name: *Rudbeckia subtomentosa*
Varietal Denomination: Little Henry

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 72 days.

(21) Appl. No.: 13/317,422

(22) Filed: Oct. 17, 2011

(51) Int. Cl.
*A01H 5/00* (2006.01)

(52) U.S. Cl. ..... Plt./474

(58) Field of Classification Search ..... Plt./474
See application file for complete search history.

*Primary Examiner* — Annette Para

(74) *Attorney, Agent, or Firm* — Klarquist Sparkman, LLP

(57) ABSTRACT

A new and distinct *Rudbeckia subtomentosa* plant named 'Little Henry' characterized by inflorescences with quilled, yellow ray florets, a medium, upright habit, and excellent vigor.

1 Drawing Sheet

Botanical denomination: *Rudbeckia subtomentosa.*
Variety designation: 'Little Henry'.

BACKGROUND OF THE INVENTION

The present invention relates to a new and distinct cultivar of *Rudbeckia subtomentosa* and given the cultivar name 'Little Henry'. *Rudbeckia* is in the family Asteraceae. This new cultivar is a whole plant mutation from tissue culture from *Rudbeckia subtomentosa* 'Henry Eilers', an unpatented plant.

Compared to *Rudbeckia subtomentosa* 'Henry Eilers', the only similar plant on the market, the new variety is much shorter and flowers 2 weeks earlier. They both have the charming quilled or tubular ray florets This new *Rudbeckia* cultivar is uniquely distinguished by:

1. inflorescences with quilled, yellow ray florets,
2. a medium, upright habit, and
3. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the inflorescences of *Rudbeckia* 'Little Henry'.

FIG. 2 shows a comparison of the habits of 4 *Rudbeckia* 'Little Henry' (left) and 1 *Rudbeckia* 'Henry Eilers' (right) on 2 year old plants in the field in full sun in mid October in Canby, Oreg.

DETAILED PLANT DESCRIPTION

The following is a detailed description of the new *Rudbeckia* cultivar based on observations of 3 year-old specimens growing in the garden in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on *The Royal Horticultural Society Colour Chart,* $5^{th}$ edition.

Plant:

*Type.*—Herbaceous perennial.
*Hardiness.*—USDA Zones 5 to 9.
*Size.*—Grows to about 121 cm wide and 45 cm tall to top of inflorescences.
*Form.*—Basal clump, with about 40 stems from the base.
*Vigor.*—Excellent.

Stem (flowering):

*Type.*—Ascending, branching where flowering only, with 5 to 12 flowers per stem.
*Size.*—To 26 cm tall to the start of a flowering branch, 7 mm wide at the base.
*Internode length.*—3 cm to 7 cm.
*Surface texture.*—Strigose.
*Color.*—Yellow Green 152B with thin vertical bands of Black 202A.

Leaf (stem):

*Type.*—Simple.
*Shape.*—Broadly ovate, ternate.
*Arrangement.*—Alternate.
*Blade size.*—Grows overall to 9.2 cm long and 9 cm wide, terminal leaflet grows to 7.5 cm long and 5 mm wide, lateral leaflets grow to 6 cm long and 3.4 cm wide.
*Margins.*—Broadly crenate.
*Apex.*—Acute.
*Base.*—Attenuate.
*Surface texture.*—Strigose on both sides.
*Venation.*—Pinnate, with 3 main veins from the base on each leaflet.
*Color.*—Topside Yellow Green 146B, veins 151C, bottom side Yellow Green 147B.
*Petiole description.*—Grows to 3.5 cm long and 2 mm wide above the clasp, strigose, Yellow Green 147C.

Inflorescence:

*Type*.—Composite with heads in loose, corymbiform to paniculiform arrays.

*Number of flowering branches from stem*.—5 to 12.

*Flowering stem*.—Grows to 40 cm tall from the start of the flowering branches to the base of the terminal inflorescence and the 2 to 6 side branches grow to 13 cm taller than the terminal; the cluster of inflorescences grows to 53 cm long and 17 cm wide; leaves on flowering branches are simple, ovate, grows to 7.5 cm long and 5 mm wide, margins serrate, base attenuate, tip acute, topside Yellow Green 146B, veins 151C, bottom side Yellow Green 147B.

*Size*.—Grows to 6 cm wide and 3 cm deep as disc enlarges.

*Form*.—Ray florets held mostly horizontally cupping to 30 degrees when older, mature disc is conic.

*Immature inflorescence*.—2 cm wide and 2 cm deep, ray florets held upright and tubular, Yellow 15C tinted Yellow Green 146B, disc color Greyed Purple 187A.

*Ray florets*.—Without pistil or stamen, ranging from 16 to 21 in number, grow to 30 mm long and 2.5 to 4 mm wide, tubular with the tip two-lobed (lobes ovate with margins entire, tips acute), top side pubescent, inside glabrous; Yellow 15B overall with topside tinted Greyed Purple 187B on veins and bottom side tinted Yellow Green 146B.

*Disc*.—Conic, becoming 12 mm deep and 15 mm wide with maturity, Brown 200A.

*Disc florets*.—About 400 in number, bisexual, each with 1 pistil and 5 stamen, grow to 6 mm long and 1.5 mm wide; corolla 3 mm long and 1.5 mm wide, tubular, glandular, 5 lobed, lobes triangular, Greyed Purple 187A on top ⅔, White NN155A on bottom ⅓; pistil 7 mm long, ovary 3 mm long, White NN155A, style 4 mm long, White NN155A on bottom to Greyed Purple 187B near top, 2-branched stigma Greyed Purple 187A; stamen 7 mm long, Greyed Purple 187A, pollen Yellow Orange 15A.

*Phyllaries*.—In 3 leafy series, area grows to 25 mm wide and 7 mm deep, lobes lanceolate in shape, reflexed, grow to 11 mm long and 2 mm wide, Green 138B, tip acuminate, margin entire, strigose on both sides.

*Receptacle*.—Grows to 5 mm wide and 8 mm deep, Yellow Green 145D.

*Bloom period*.—August through October in Canby, Oreg.

*Fragrance*.—None.

*Lastingness*.—Each inflorescence lasts about two to three weeks in Canby, Oreg.

Seeds: None seen.

*Fertility*.—Poor.

Disease and pests: No known resistances.

I claim:

1. A new and distinct *Rudbeckia* plant as herein illustrated and described.

* * * * *

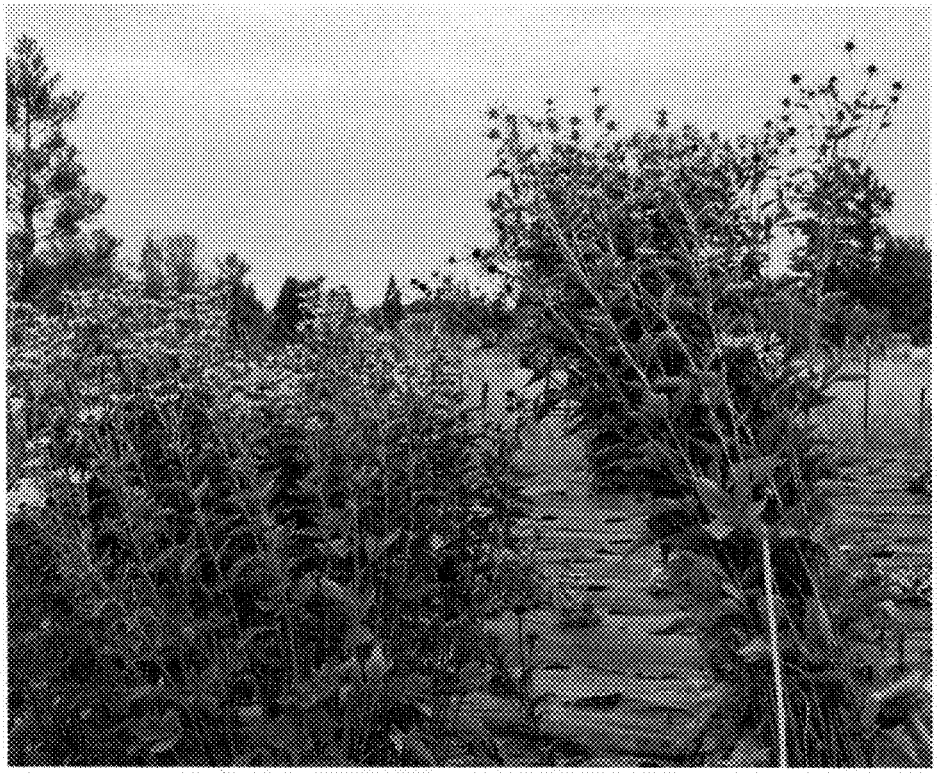

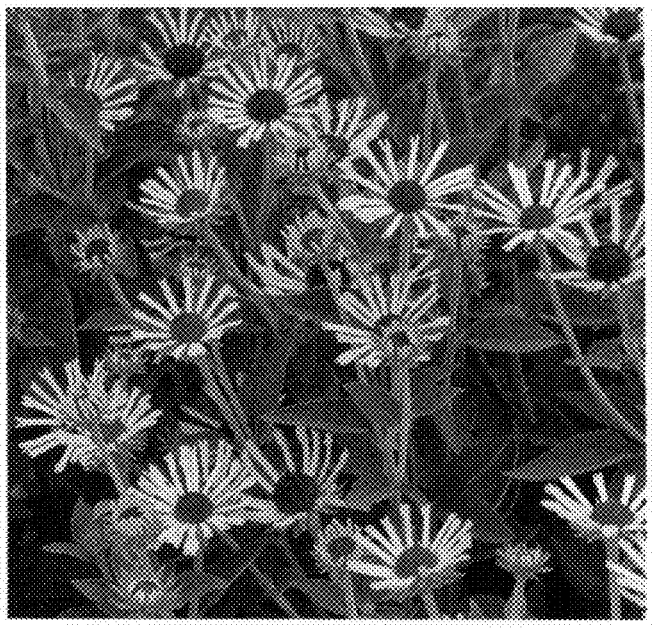
FIG. 1 above, FIG. 2 below